(12) United States Patent
Tsai et al.

(10) Patent No.: US 8,455,254 B2
(45) Date of Patent: *Jun. 4, 2013

(54) METHOD OF ACCELERATING OSTEOGENIC DIFFERENTIATION AND COMPOSITION THEREOF

(75) Inventors: Yu-Hui Tsai, Banciao (TW); Li-Hsuan Chiu, Taipei (TW)

(73) Assignee: Taipei Medical University, Taipei (TW)

( * ) Notice: Subject to any disclaimer, the term of this patent is extended or adjusted under 35 U.S.C. 154(b) by 448 days.

This patent is subject to a terminal disclaimer.

(21) Appl. No.: 12/799,345

(22) Filed: Apr. 22, 2010

(65) Prior Publication Data

US 2011/0262403 A1    Oct. 27, 2011

(51) Int. Cl.
*C12N 5/00* (2006.01)
(52) U.S. Cl.
USPC .......................................... 435/377; 435/395
(58) Field of Classification Search
None
See application file for complete search history.

(56) References Cited

U.S. PATENT DOCUMENTS 5,736,396 A * 4/1998 Bruder et al. ................. 435/366
5,824,084 A * 10/1998 Muschler ...................... 128/898

OTHER PUBLICATIONS

Yoneno et al, J Biomed Mater Res, 2005, vol. 75A, pp. 733-741.*
Mizuno et al, J Biomed Mater Res, 2001, vol. 56, pp. 368-375.*

* cited by examiner

*Primary Examiner* — Allison Ford
(74) *Attorney, Agent, or Firm* — Hudak, Shunk & Farine Co. LPA

(57) ABSTRACT

The invention discloses a method of accelerating osteogenic differentiation and a composition thereof. The method comprises a step of adding type II collagen into stem/progenitor cells or osteoblasts to accelerate the osteogenic differentiation of the added cells, and the composition comprises type II collagen, and stem/progenitor cells or osteoblasts. Type II collagen can accelerate osteogenesis of mesenchymal stem cells (MSCs) much faster than does type I collagen. The said composition is effective to facilitate bone repair upon introduction of the composition into various osseous defects.

16 Claims, 3 Drawing Sheets

METHOD OF ACCELERATING OSTEOGENIC DIFFERENTIATION AND COMPOSITION THEREOF

FIELD OF THE INVENTION

The present invention relates to a field of bone regeneration, and in particular to a method of accelerating osteogenic differentiation and a composition thereof.

BACKGROUND

For vertebrates, such as mammals, birds and fishes, bones are an excessively hard tissue for providing support and protection from physical stress. The bone is a hardened connective tissue which is composed of cells and extracellular matrices (ECMs). Different from other connective tissue, the matrices of bone tissue are mineralized. In case that bone tissue fails to repair itself at a normal rate, or that bone loss occurs as a result of injuries or diseases, it may lead to disability, and huge waste of time and money. Osteogenesis, the growth of new bone, is a part of the normal healing process which involves the recruitment and activation of osteoblasts and mesenchymal stem cells (MSCs). In the elderly, osteogenesis after disease or severe trauma can be a slow process. Thus, it is an important issue in this field to accelerate osteogenesis and speed the healing process after trauma and orthopaedic or dental procedures.

Endochondral ossification is one of the two essential processes during the embryonic development of long bones and the natural healing of fractures. Unlike intramembranous ossification, which dominates the rudimentary formation of cranium, cartilage is present during the endochondral ossification process. It is a highly coordinated, multi-step process. Briefly, cascades of events participated in this developmental process includes MSC condensation, chondrocyte differentiation/maturation/hypertrophy, cartilage template mineralization, and the consequent invasion and differentiation of the osteo-progenitor cells. Extracellular matrix components have also been demonstrated to play crucial roles in coordinating and directing MSC differentiation. This interaction triggers the differentiation of MSCs or osteo-progenitor towards osteogenesis, and leads to the mineralization of the tissue into mature bone structure.

As is known, type I collagen enhances osteogenesis of human MSCs and osteoblasts. Upon their attachment to the type I collagen-coated surface, the stimulated osteogenic differentiation of these cells can be mediated via an ERK1/2 signaling pathway. For this reason, the existing application to type I collagen is mostly to mix type I collagen with calcium phosphate to fabricate scaffolds as bone filling materials. However, no report has addressed on the modulating effect of type II collagen in promoting osteogenesis. Type II collagen is mainly presented in the cartilage as well as in the developing bone, and is largely considered as a cartilaginous ECM in previous studies. Therefore, type II collage is rarely discussed about its mechanism and importance in the process of osteogenesis, and is also not being applied to the promotion of bone formation.

SUMMARY

One aspect of the present invention is to provide a method of accelerating osteogenic differentiation, comprising that type II collagen is added into tissue cells including stem cells, progenitor cells and osteoblasts so as to accelerate the osteogenic differentiation of the tissue cells, wherein the stem cells and progenitor cells have a spontaneous tendency toward the osteogenic differentiation. This method can be applied to cell differentiation fields, such as in vitro culture of bone cells, and osteo-induction of stem cells.

In another aspect of the present invention, a composition is provided for accelerating osteogenic differentiation, comprising type II collagen and tissue cells including stem cells, progenitor cells, and osteoblasts in an osteogenic medium made of $10^{-10}$-$10^{-7}$ M dexamethason, 5-50 mM β-glycerolphosphate, and 10-200 μg/ml ascorbic acid in Dulbecco's Modified Eagle Medium-low glucose (DMEM-LG), wherein the stem cells and progenitor cells have a spontaneous tendency toward the osteogenic differentiation.

In accordance with the present invention, the method of accelerating osteogenic differentiation and the composition thereof may have one or more advantages as follows:

(1) The required type II collagen in the present invention is easily available. For example, type II collagen can be manufactured by genetic recombination of type II collagen cDNA, such as human type II collagen cDNA, or by extraction and purification from a cartilage tissue of an animal comprising poultry, livestock or fishes.

(2) Type II collagen according to the present invention can activate $ERK_{1/2}$ and JNK signaling pathways, thereby enhancing the bone deposition of the stem cells having a tendency toward the osteogenic differentiation, or further elevating the activity of alkaline phosphatase (ALP). Compared to the known type I collagen, the composition comprising type II collagen not only can accelerating calcium deposition, but also quickly increase the amount of the bone deposition so as to achieve fast bone regeneration. Therefore, the present invention has the potential for clinical applications to bone repair.

(3) For the sake of facilitating bone repair and regeneration, type II collagen in the present invention can be used alone, or be mixed with the stem cells, progenitor cells or osteoblasts to achieve the desired effect.

(4) During the healing process, the added type II collagen may stimulate certain cell populations to form new bone tissue which serve to replace the lost or damaged tissues. Such type II collagen has potential to use in clinical situations where skeletal tissue regeneration is necessary to restore normal function, for example, at sites of bone trauma and sites of periodontal defects.

BRIEF DESCRIPTION OF THE DRAWINGS

The exemplary embodiments of the present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

Figure 1:
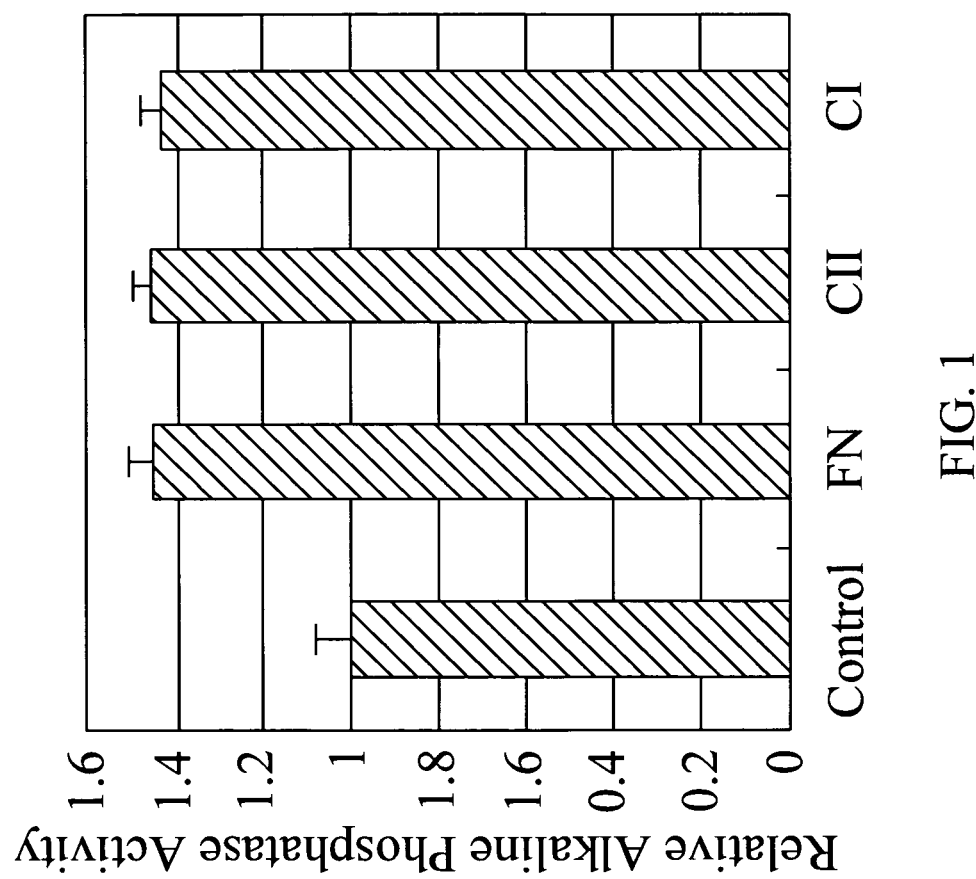
FIG. 1 illustrates the ALP activities of U2OS osteoblast cells cultured on various ECM components in the osteogenic medium for 7 days, wherein the ECM components in this figure include Fibronectin (FN), type II collagen (CII) and type I collagen (CI) as compared to non-coated surface (control)

As used herein, the term "type II collagen" not only refers to type II collagen itself, but also refers to its biologically active fragment and analogue.

As used herein, the processes of the bone repair and regeneration include cell proliferation, cell differentiation, matrix remodeling and angiogenesis.

The present invention provides a method of accelerating osteogenic differentiation, comprising adding type II collagen into tissue cells selected from the group consisting of stem cells, progenitor cells and osteoblasts so as to accelerate the osteogenic differentiation of the tissue cells. For instance, type II collagen can be directly applied at bone fracture sites to stimulate the osteogenic differentiation of the osteoblasts, mesenchymal stem cells (MSCs), and mesenchymal progenitor cells (MPCs) in the vicinity, and to facilitate bone repair and regeneration of the wound.

The present invention also provides a composition for accelerating osteogenic differentiation, comprising type II collagen and tissue cells selected from the group consisting of stem cells, progenitor cells and osteoblasts in an osteogenic medium made of $10^{-10}$-$10^{-7}$ M dexamethason, 5-50 mM β-glycerolphosphate, and 10-200 µg/ml ascorbic acid in Dulbecco's Modified Eagle Medium-low glucose (DMEM-LG).

Wherein, the stem cells and progenitor cells have a tendency toward the osteogenic differentiation. Preferably, the stem cells may be mesenchymal stem cells obtained from bone marrow, umbilical cord blood or other somatic tissues, stem cells obtained from baby teeth or permanent teeth, or embryonic stem cells; the progenitor cells may be mesenchymal progenitor cells obtained from bone marrow, umbilical cord blood or other somatic tissues. Type II collagen is about 5-1000 µg/ml, preferably 20-200 µg/ml, of the concentration for coating the surface attached by the tissue cells, or about 100 to 600 µg/ml for including in cell differentiation culture, and is obtained by genetic recombination of type II collagen cDNA, or by extraction and purification from a cartilage tissue of an animal comprising poultry, such as chicken and duck; livestock, such as pig, cattle and sheep; or fishes.

Optionally, in order to accelerate osteogenic differentiation of the cells, a growth factor may be further added as a regulator of bone repair and regeneration, such as bone morphogenetic protein (BMP), transforming growth factor-β (TGF-β), fibroblast growth factor (FGF), insulin-like growth factor (IGF-I), vascular endothelial growth factor (VEGF), and platelet derived growth factor (PDGF). Preferably, BMP is BMP-2, and TGF-β is TGF-β1.

EXAMPLES

The present invention will be better understood by reference to the following Examples, which are provided as exemplary embodiments of the invention, and not by way of limitation.

Example 1

Type II Collagen Up-Regulating Alp Activity in Osteoblast Cell Lines

In this example, the modulating effects of type II collagen (CII), type I collagen (CI) and fibronectin (FN) on alkaline phosphatase (ALP) enzyme activity are examined in two different osteoblast cell lines, U2OS and MG63.

Culture Dish Coating

Cover slips or tissue culture dishes are coated with purified ECM components (type II collagen, type I collagen, or fibronectin) or poly-L-lysine (as control in experiments using cover slips) at a concentration of 5-1000 µg/ml, preferably 20-200 µg/ml, more preferably 20 µg/ml, for 2 hours at room temperature. After incubation, the remaining ECM solutions are removed. The dishes or cover slips are further washed with phosphate-buffered saline (PBS) followed by incubation with 5% BSA in PBS for 30 minutes. The coated dishes are UV-sterilized and then stored in 4° C. until use.

Alkaline Phosphatase Activity Assay

U2OS and MG63 osteoblast cells are plated on dishes coated with various ECM components for 7 days, and then the cells are subjected to ALP enzyme activity assay. ALP enzyme activity of the cultured osteoblasts is detected after cells are rinsed with 50 mM, pH 10.5 glycine buffer. The cells are then incubated with 1 mg/ml p-nitrophenyl phosphate (pNPP) dissolved in pH 10.5 glycine buffer containing 1 mM $MgCl_2$ at 37□ for 3 hours. ALP converts pNPP into a yellow color product and the relative enzyme activity is assessed at absorbance of 405 nm wavelength in a spectrophotometer.

Figure 2:
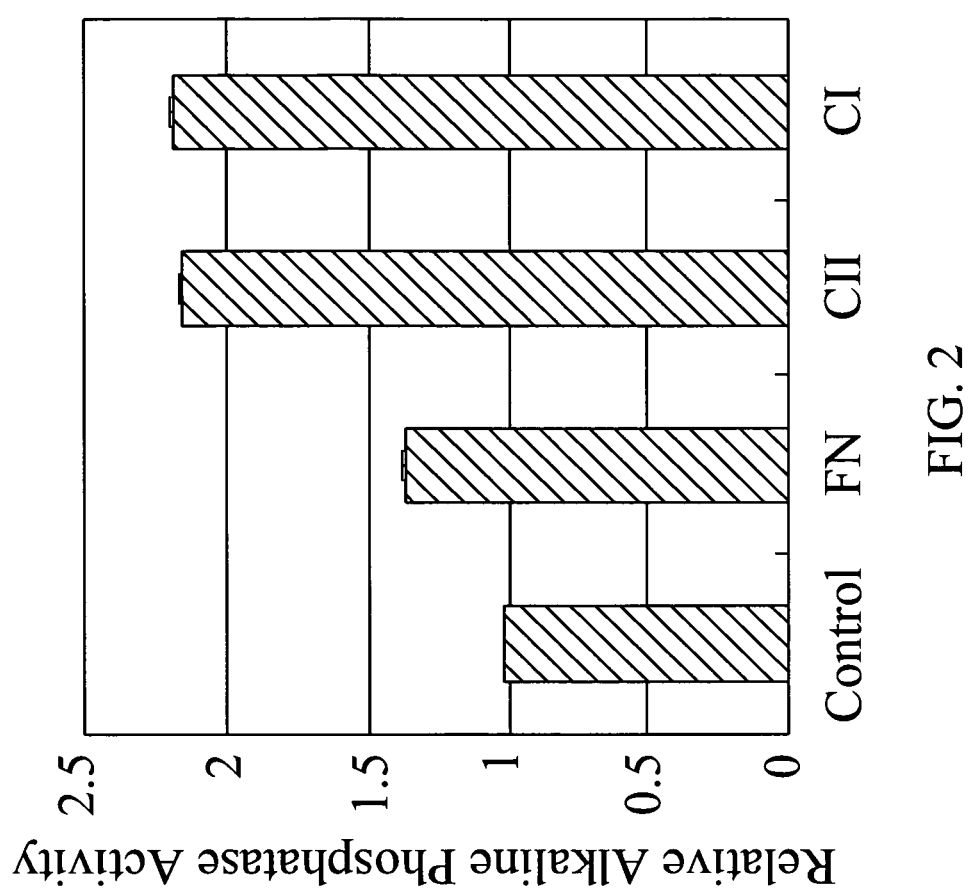
FIG. 2 illustrates the ALP activities of MG63 osteoblast cells cultured on various ECM components in the osteogenic medium for 7 days, wherein the ECM components in this figure include Fibronectin (FN), type II collagen (CII) and type I collagen (CI) as compared to non-coated surface (control)

FIG. 1 and FIG. 2 show the effects of various ECM components on ALP activities of U2OS osteoblast cells and MG63 osteoblast cells, respectively. As shown in the figures, the ECM components stimulate ALP activity of U2OS cells at the end of 7 day culture in the osteogenic medium. Type II collagen-coated plates constantly exhibit an elevated ALP activity in the both cell lines to 1.4- to 2-fold levels as comparing to those in cells grown on the non-coated control plates. This example, especially in the MG63 cells, demonstrates that the induction potency of type I collagen (CI) and type II collagen (CII) is greater than that of fibronectin (FN) for activation of ALP activity.

Example 2

The Effect of Type II Collagen on Mesenchymal Stem Cell (MSC) Calcium Deposition In this example, the modulating effects of type II collagen-coated surface (CII), type I collagen-coated surface (CI), and a 1:1 ration mixture of type II collagen and type I collagen-coated surface (CI+CII) on calcium deposition ability of mesenchymal stem cell (MSC) are examined.

MSC Isolation, Cultivation & Storage

Bone marrow aspirates are obtained aseptically from donors (18~65-year-old) who receive femoral or iliac surgery. Bone marrow is aspirated using a 10 ml syringe. The aspirates are immediately mixed with sodium-heparin, and diluted in five volumes of phosphate-buffered saline (PBS). The cell suspension is then fractionated by overlay on a percoll gradient (40% initial density, Pharmacia) and centrifuged. The MSC-enriched interface fraction is collected and plated in a 10-cm dish containing 10 ml Dulbeccos Modified Eagles Medium with 1 mg/ml glucose (DMEM/LG, Sigma D5523), 10% FBS, 1× penicillin/streptomycin/fungizone. The medium is changed every four days. When cells reach 80% confluence, they are trypsinized and passaged into new 10-cm dishes at a cell density of $5\times10^5$ cells/dish.

Surface Coating

Tissue culture dishes are coated with type I collagen, type II collagen, or the mixture of type I and type II collagen (1:1 ration) at a concentration of 5-1000 µg/ml, preferably 20-200 µg/ml, more preferably 20 µg/ml, for 2 hours at room temperature. After incubation, the remaining ECM solution is removed. The collagen-coated dishes are further washed with PBS. The coated dishes are then UV-sterilized and stored at 4° C. till use.

Calcium Deposition Assay Using Alizarin Red S Staining

MSCs are plated on type I collagen-coated (CI), type II collagen-coated (CII), type I and type II collagen mixture (1:1 ration)-coated (CI+CII) or non-coated control culture dishes. After attached, cells are then treated with osteogenic medium, made of $10^{-7}$ M dexamethason, 10 mM β-glycerolphosphate, and 50 µg/ml ascorbic acid in DMEM-LG, to induce osteogenic differentiation. Cells are harvested at day 4, 8, 12 and 16, and subjected to alizarin staining. To detect calcium deposition on the cell layer of differentiated MSCs, cells are rinsed rapidly with distilled water. Then, 1 ml of pH 4.2 Alizarin Red S solution is added to cover cell surface for 5 minutes followed by washing thoroughly with distilled water. The calcium deposits exhibit orange red coloration on the cell surface, and are recorded photographically or microscopically.

Figure 3:
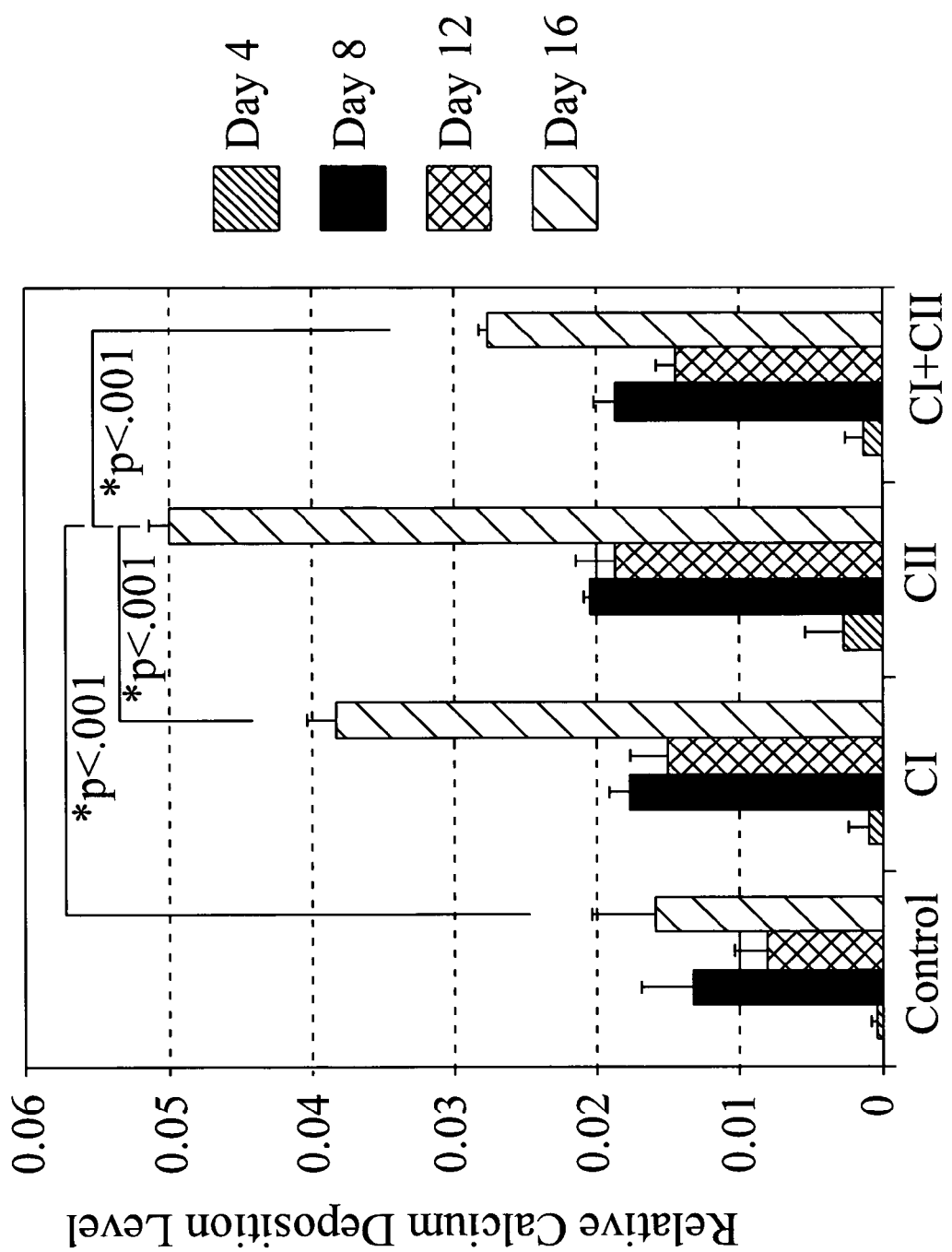
FIG. 3 illustrates the calcium deposition levels of MSCs cultured on the non-coated (Control), type I collagen-coated (CI), type II collagen-coated (CII), and type I/type II collagen (1:1) mixture-coated surfaces in the osteogenic medium for 4, 8, 12, 16. The longer the culture duration, the greater effect of type II collagen on calcium deposition of MSCs is observed.

FIG. 3 shows the calcium deposition level of MSCs to illustrate the modulating effects of type II collagen (CII) and type I collagen (CI) on mesenchymal stem cell (MSC) osteogenesis. In the figure, monolayer MSCs are cultured on variously coated dishes. Cells are cultured on type II collagen-coated (CII), type I collagen (CI)-coated, type II and type I collagen mixture (1:1 ration)-coated (CI+CII) and non-coated control culture dishes in osteogenic medium for 4, 8, 12 and 16 days. Cells are then fixed and subjected to Alizarin Red S staining for the detection of calcium deposition. At day 16, cells in type II collagen-coated groups exhibit a 3.33 fold higher calcium deposition level than those in the type I collagen-coated group, control group, and even type I and type II mixture-coated group. This result addresses that type II collagen-coated surface accelerates calcium deposition of MSCs in osteogenic medium. It is concluded that in addition to enhancing osteoblasts maturation, type II collagen also accelerates MSC differentiation.

While particular embodiments of the present invention have been shown and described, it will be obvious to those skilled in the art that, based upon the teachings herein, changes and modifications may be made without departing from this invention and its broader aspects. Therefore, the appended claims are intended to encompass within their scope of all such changes and modifications as are within the true spirit and scope of the exemplary embodiments of the present invention.

What is claimed is:

1. A method of accelerating osteogenic differentiation, comprising providing isolated type II collagen as a substrate coating for tissue cells selected from the group consisting of stem cells, progenitor cells and osteoblasts so as to accelerate the osteogenic differentiation of the tissue cells, wherein the stem cells and progenitor cells have a tendency toward osteogenic differentiation.

2. The method of claim 1, wherein the type II collagen is obtained by genetic recombination of type II collagen cDNA, or by extraction and purification from a cartilage tissue of an animal selected from the group consisting of poultry, livestock and fishes.

3. The method of claim 1, wherein the stem cells comprise mesenchymal stem cells obtained from bone marrow, umbilical cord blood or other somatic tissues; stem cells obtained from baby teeth or permanent teeth; or embryonic stem cells.

4. The method of claim 1, wherein the progenitor cells comprise mesenchymal progenitor cells obtained from bone marrow, umbilical cord blood or other somatic tissues.

5. The method of claim 1, wherein the concentration of type II collagen in the substrate coating is in a range of 5 to 1000 µg/ml.

6. The method of claim 1, wherein the concentration of the type II collagen in the substrate coating is in a range of 20 to 200 µg/ml.

7. The method of claim 1, further comprising a step of providing a growth factor to the tissue cells as a regulator of bone repair and regeneration.

8. The method of claim 7, wherein the growth factor comprises bone morphogenetic protein (BMP), transforming growth factor-β (TGF-β), fibroblast growth factor (FGF), insulin-like growth factor (IGF-I), vascular endothelial growth factor (VEGF), or platelet derived growth factor (PDGF).

9. A composition for accelerating osteogenic differentiation, comprising:
  isolated type II collagen as a substrate coating;
  tissue cells selected from the group consisting of stem cells, progenitor cells and osteoblasts, wherein the stem cells and progenitor cells have a tendency toward osteogenic differentiation; and
  osteogenic medium made of $10^{-10}$-$10^{-7}$ M dexamethasone, 5-50 mM β-glycerolphosphate, and 10-200 µg/ml ascorbic acid in Dulbecco's Modified Eagle Medium-low glucose (DMEM-LG).

10. The composition of claim 9, wherein the type II collagen is obtained by genetic recombination of type II collagen cDNA, or by extraction and purification from a cartilage tissue of an animal selected from the group consisting of poultry, livestock and fishes.

11. The composition of claim 9, wherein the stem cells comprise mesenchymal stem cells obtained from bone marrow, umbilical cord blood or other somatic tissues; stem cells obtained from baby teeth or permanent teeth; or embryonic stem cells.

12. The composition of claim 9, wherein the progenitor cells comprise mesenchymal progenitor cells obtained from bone marrow, umbilical cord blood or other somatic tissues.

13. The composition of claim 9, wherein the concentration of the type II collagen in the substrate coating is in a range of 5 to 1000 µg/mL.

14. The composition of claim 9, wherein the concentration of the type II collagen in the substrate coating is in a range of 20 to 200 µg/ml.

15. The composition of claim 9, further comprising a growth factor as a regulator of bone repair and regeneration.

16. The composition of claim 15, wherein the growth factor comprises bone morphogenetic protein (BMP), transforming growth factor-β (TGF-β), fibroblast growth factor (FGF), fibroblast insulin-like growth factor (IGF-I), vascular endothelial growth factor (VEGF), or platelet derived growth factor (PDGF).

* * * * *